US006437328B1

(12) United States Patent
Knauss et al.

(10) Patent No.: US 6,437,328 B1
(45) Date of Patent: Aug. 20, 2002

(54) HYPERBARIC HYDROTHERMAL ATOMIC FORCE MICROSCOPE

(75) Inventors: Kevin G. Knauss, Livermore; Carl O. Boro, Milpitas, both of CA (US); Steven R. Higgins; Carrick M. Eggleston, both of Laramie, WY (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/366,902

(22) Filed: Aug. 3, 1999

Related U.S. Application Data

(60) Provisional application No. 60/095,165, filed on Aug. 3, 1998.

(51) Int. Cl.[7] .............................................. G01N 13/16
(52) U.S. Cl. ..................................... 250/306; 250/307
(58) Field of Search .................................. 250/306, 307

(56) References Cited

U.S. PATENT DOCUMENTS

| | | | |
|---|---|---|---|
| 5,200,616 A | | 4/1993 | Kokawa et al. ............. 250/306 |
| 5,291,775 A | * | 3/1994 | Gamble et al. ............. 250/306 |
| 5,410,910 A | | 5/1995 | Somlyo et al. ............... 73/105 |
| 5,654,546 A | * | 8/1997 | Lindsay ...................... 250/306 |
| 5,750,989 A | | 5/1998 | Lindsay et al. ............. 250/306 |

OTHER PUBLICATIONS

Temperature Controlled Microstage For An Atomic Force Microscope, I. Musevic et al., Rev. Sci. Instrum. vol. 67, No. 7, Jul. 1996, pp. 2554–2556.

Ann In–Situ Hot Stage For Temperature Dependent Tapping–Model Atomic Force Microscopy, S.G. Prilliman et al., Submitted To Review Of Scientific Instruments May 25, 1998. Accepted for publication Jun. 25, 1998, pp. 1–8.

Dissolution Of Baryte (001) Observed By Hydrothermal Scanning Force Microscopy, G. Jordan et al., Goldschmidt Conference, Toulouse 1998, Mineralogical Magazine, vol. 62A, pp. 725–726.

In–Situ Observation Of Oxide And Silicate Mineral Dissolution By Hydrothermal Scanning Force Microscopy: Initial Results For Hematite and Albite, S.R. Higgins et al., Goldschmidt Conference, Toulouse 1998, Mineralogical Magazine, vol. 62A, pp. 618–619.

Dissolution Kinetis Of The Barium Sulfate (001) Surface By Hydrothermal Atomic Force Microscopy, S.R. Higgins et al., Langmuir 1998, vol. 14, pp. 4967–4971.

A Hydrothermal Atomic Force Microscope For Imaging In Aqueous Solution Up To 150° C[a], S.R. Higgins, et al., Review Of Scientific Instruments, vol. 69, No. 8, Aug. 1998, pp. 2994–2998.

* cited by examiner

*Primary Examiner*—Bruce Anderson
(74) *Attorney, Agent, or Firm*—L. E. Carnahan; Alan H. Thompson

(57) ABSTRACT

A hyperbaric hydrothermal atomic force microscope (AFM) is provided to image solid surfaces in fluids, either liquid or gas, at pressures greater than normal atmospheric pressure. The sample can be heated and its surface imaged in aqueous solution at temperatures greater than 100° C. with less than 1 nm vertical resolution. A gas pressurized microscope base chamber houses the stepper motor and piezoelectric scanner. A chemically inert, flexible membrane separates this base chamber from the sample cell environment and constrains a high temperature, pressurized liquid or gas in the sample cell while allowing movement of the scanner. The sample cell is designed for continuous flow of liquid or gas through the sample environment.

16 Claims, 4 Drawing Sheets

HYPERBARIC HYDROTHERMAL ATOMIC FORCE MICROSCOPE

This patent application claims the benefit of priority of U.S. Provisional Patent Application Ser. No. 60/095,165, filed Aug. 3, 1998.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to an atomic force microscope capable of imaging surfaces in fluids at pressures greater than normal atmospheric pressure. More particularly, the surfaces can be imaged in gas or liquid at temperatures greater than 100° C.

2. Description of Related Art

Scanning probe microscopy, particularly atomic force microscopy (AFM), has become an indispensable tool for imaging solid surfaces at resolutions ranging from the atomic scale (for periodic and defect structures) to the microtopographic scale (for roughness, particle analysis, step-terrace patterns, magnetic patterns, microorganisms and biomolecules). AFM is also important for crystal growth studies because it allows not only ex-situ characterization of the spacing and shape of atomic scale steps and terraces, but also in-situ, real-time imaging of step motion and surface kinematics during crystal dissolution or growth in aqueous or other solutions.

A limitation of AFM has been the relatively narrow range of temperatures accessible for in-situ imaging in liquids. The range of crystal dissolution or growth rates accessible to in-situ AFM imaging of step motion is about $10^{-6}$ to $10^{-10}$ moles $m^{-2}s^{-1}$. Rates of most oxides and silicates (which are of interest in chemical weathering of rocks, buildings and monuments, radioactive waste storage, industrial pipe scaling, and enhanced oil recovery techniques such as steam-flooding, and other applications) are below this range at room temperature. To apply AFM to the aqueous dissolution and growth of these materials, higher temperatures are needed to hasten the reaction rates. For example, the minimum dissolution rates (dependent on pH) of quartz (crystalline $SiO_2$) and albite ($NaAlSi_3O_8$) are higher than $10^{-10}$ moles $m^{-2}s^{-1}$ at 150° C.

Heating stages for ambient AFM have been built (see Musevic et al., Rev. Sci. Instrum. 67, 2554–2556 (1996); Prilliman et al., Rev. Sci. Inst., 69, 3245–3250 (1998) (at http://nanonet.rice.edu/papers/Rev-Sci-Inst-TM-AFM-Heating/)). However, the vapor pressure of the liquid phase imposes a fundamental limitation on fluid cell temperature; a 100° C. aqueous solution will boil if the pressure is not greater than the vapor pressure of water at temperature. Moreover, practical temperature limits can be significantly lower than the boiling point of the solution. Exsolution (e.g., of dissolved $CO_2$ and $O_2$) and bubble formation interferes with imaging unless the source solution is degassed upstream of the AFM sample cell; this is generally accomplished by overheating at the source, which means, if pressurization is not possible, that the sample cell temperature must be lower than the ambient boiling point. In addition, some experiments (such as dissolution or growth of carbonates) requires use of dissolved gases, so that bubble formation rather than boiling imposes a temperature limit.

A need exists for an AFM that allows observation of atomic scale phenomena in liquids or gases at temperatures and pressures not currently attainable. The present invention is a design of an AFM capable of imaging in aqueous solution or other fluids at temperatures greater than 100° C. and at pressures greater than normal atmospheric pressure.

SUMMARY OF THE INVENTION

The object of the present invention is to provide an atomic force microscope (AFM) that can be used to image solid surfaces in fluids, either liquid or gas, at pressures greater than normal atmospheric pressure. Surfaces can be imaged in fluids at temperatures greater than 100° C. and greater than 1 atmosphere, with less than 1 nanometer vertical resolution.

Internal pressurization of the microscope is achieved in two separate chambers: the base chamber and the sample cell. The AFM has a gas pressurized microscope base chamber, which houses the stepper motor for coarse advance and the piezoelectric scanner. A chemically inert, flexible membrane separates this base chamber from the sample cell and constrains a high temperature, pressurized liquid or gas in the sample cell, while allowing three-dimensional motion of the sample by means of the piezoelectric scanner element. The membrane prevents any fluid from leaking from the sample cell into the gas pressurized base chamber. All electromechanical and mechanical components are reliably separated from any liquid in the sample cell.

The sample cell has inlet and outlet ports for the continuous flow of gas or liquid through the sample environment; other ports can be added for various probes, such as a temperature transducer or pH monitor. Fluid flow through the sample cell is controlled by means of a back-pressure regulator or mass flow controller. An optically transparent window on the sample cell allows an AFM laser optical head to be used for detection of cantilever deflections inside the sample cell. Resistive heating is used to maintain isothermal conditions in the sample cell. In an alternative embodiment, a second fluid cell and membrane are situated between the sample cell and the base chamber. The second cell can be used to prevent bubble formation in the sample cell caused by gas permeating from the gas pressurized base chamber through the membrane into the sample chamber.

The present invention overcomes current limitations on the temperature and pressure range accessible to AFM imaging, particularly in aqueous solutions under hydrothermal conditions. Immediate applications of this AFM include the study of surface chemical and redox reactions at nanometer scales and at temperatures sufficient to increase the net reaction rates for many materials so as to be observable by atomic force microscopy. This invention is of interest in the fields of geochemistry, environmental science, materials science such as semiconductor device manufacturing, and other areas of manufacturing that use processes occurring at the nanometer scale. Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

Figure 1:
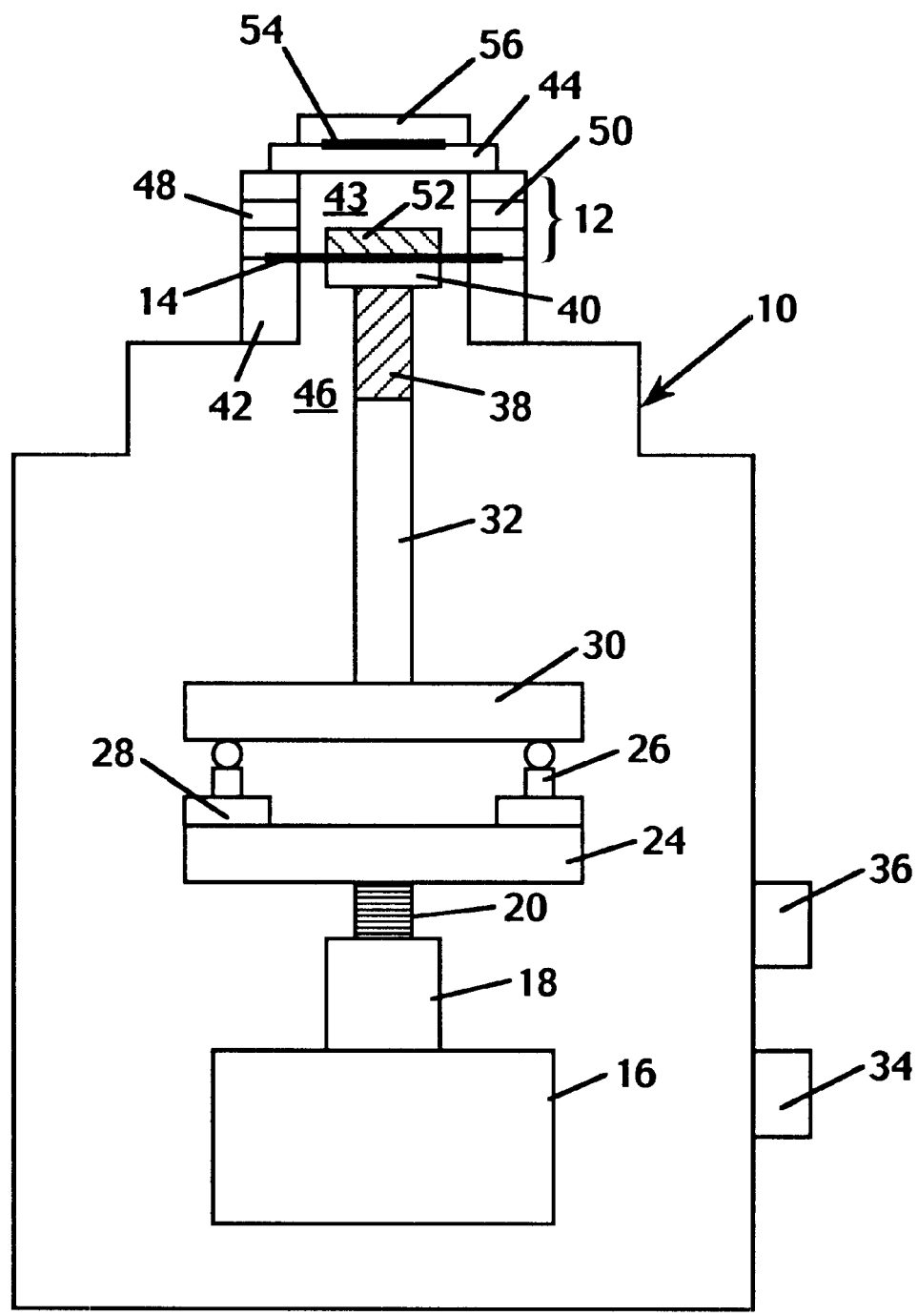
FIG. 1 is a schematic of a hyperbaric hydrothermal AFM according to the present invention.

The present invention is an atomic force microscope (AFM) capable of imaging solid surfaces in a fluid, either liquid or gas, at elevated pressures, i.e., pressures greater than normal atmospheric pressure. Using this AFM, surfaces can be imaged in liquids (e.g., aqueous solutions) or gases at temperatures greater than 100° C. and greater than 1 atmosphere with less than 1 nm vertical resolution. FIG. 1 shows an AFM according to the present invention. The AFM has a base chamber 10 that is capable of containing a pressurized gas and contains the mechanical and electromechanical components for scanning the sample. The sample cell 12 is mounted to the base chamber, and a flexible membrane 14 separates the base chamber 10 gas environment from the sample cell 12 fluid environment.

The base chamber 10 contains the stepper motor and housing 16 and other coarse advance mechanisms. The motor 16 is connected, for example, to a flexible shaft coupling 18 and a leadscrew 20. Upon rotation of the leadscrew 20, a leadscrew advance plate 24 advances or retracts. Linear shafts 26 and bearings 28 permit leadscrew advance of a scanner base plate 30, which is connected to a piezoelectric scanner 32.

The base chamber 10 includes a port 34 to introduce (and discharge) a gas to pressurize the chamber 10. The gas is an inert gas, such as nitrogen ($N_2$) or argon. The chamber 10 also has at least one port 36 for high pressure electrical feed-throughs, through which the control signals for the stepper motor 16 and piezoelectric scanner 32 are carried. A spacer 38 atop the scanner 32 provides thermal isolation of the scanner 32 from the heated sample cell 12 The spacer 38 is typically made of an insulating material, such as alumina.

The base chamber 10 can be constructed of a material such as stainless steel or aluminum, or with a low coefficient of thermal expansion, such as invar. Heat flow to the base chamber 10 may cause additional thermal expansion and drift. The piezoelectric ceramic scanner (e.g., lead zirconate titanate or PZT) has a Curie temperature of 350° C. and only a slight change in sensitivity between 80° C. and 220° C. Because the PZT is typically separated from the sample cell by a spacer 38, it heats up less than the sample cell. Thus, the PZT Curie temperature does not necessarily represent a fundamental limiting temperature for the sample cell.

Figure 2:
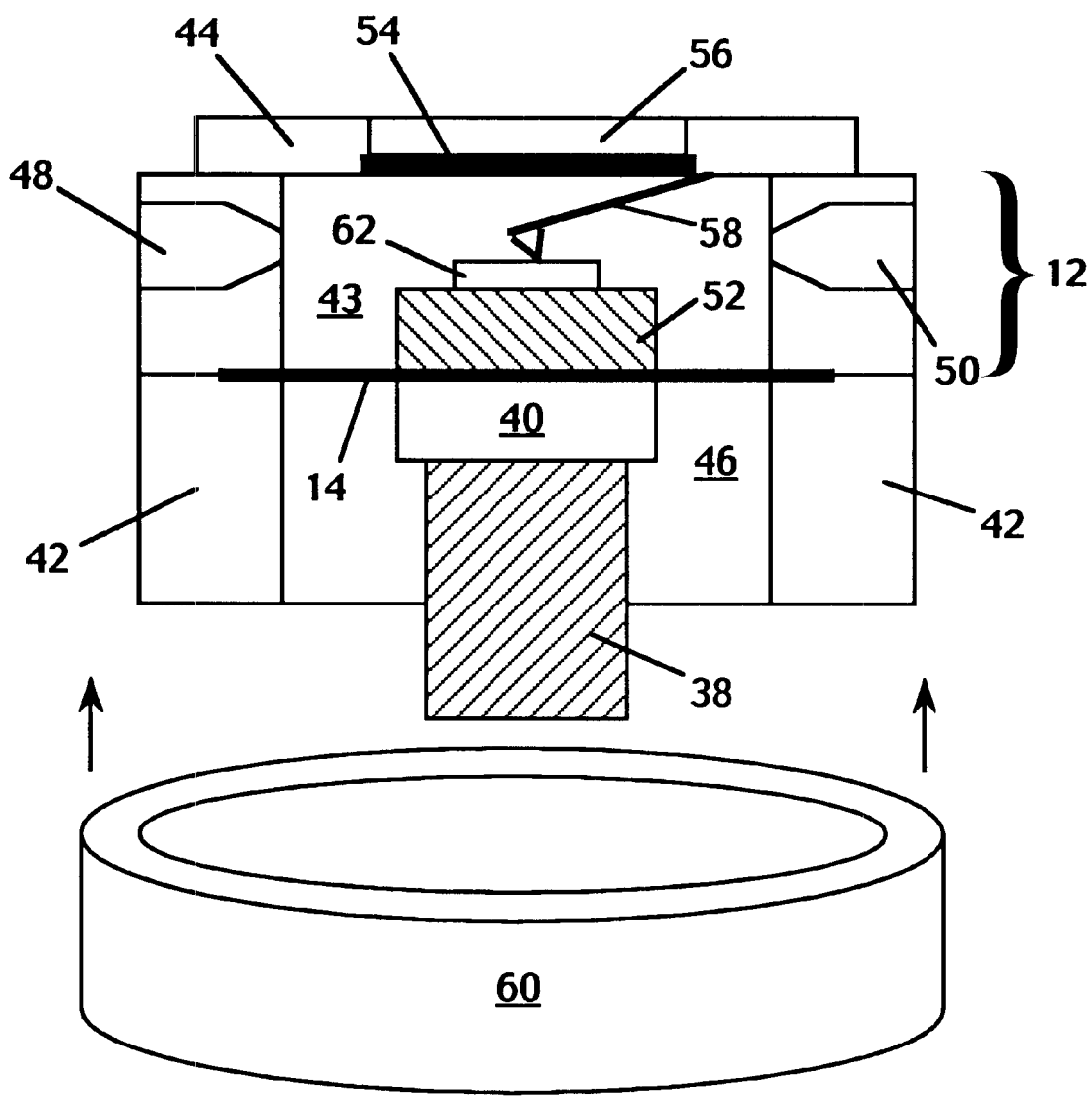
FIG. 2 is a schematic of the flow-through sample cell according to the present invention.

Atop the piezoelectric scanner 32 and scanner spacer 38 is a backing plate 40, typically made of metal. Referring to FIG. 2, the backing plate 40 and scanner spacer 38 are surrounded by an insulating spacer 42. The spacer 42 may be made from a material that is chemically resistant and rigid, such as a fluorohydrocarbon (e.g., Kel-F™). The sample cell 12 is positioned on top of the insulating spacer 42, and the sample environment 43 is separated from the gas pressurized microscope base chamber 10 environment 46 by a chemically inert membrane 14.

The membrane 14 is sealed between the sample cell 12 and the backing plate 40. The membrane 14 is flexible and thus made from a material that is elastic or reversibly deformable. The membrane 14 must be flexible enough to allow the piezoelectric scanner 32 to move in all directions.

The scanner 32 is made from a fragile ceramic that cracks easily under stress. The only external forces the scanner 32 experiences are uniformly distributed on all of its surfaces and are due to the pressure applied to the base chamber 10 of the microscope.

The membrane 14 must be chemically inert or resistant, since the membrane 14 is in direct contact with the fluid in the sample cell 12. Suitable flexible, inert materials include elastomers, such as perfluoro elastomers (Kalrez™), or foils made of a noble metal such as gold. The membrane 14 can be any thickness, but must be thin enough to be flexible (e.g., about 250 $\mu$m thick), as the membrane 14 may bow or distend. However, the membrane 14 must also be strong enough to protect the piezoelectric scanner 32 from coming into direct contact with the liquids or otherwise reactive fluids from the sample cell 12 an event that would cause scanner 32 failure. The membrane 14 is fairly impermeable to the gases in the base chamber 10, the lack of a pressure gradient between the sample cell 12 and the base chamber 10 produces no significant net movement of gas from the base chamber 10 to the sample cell 12 A significant pressure differential across the membrane 14 would cause it to burst.

Pressurization and heating change the apparent stiffness of the membrane 14, leading to changes in scanner 32 sensitivity. Because any change to the membrane affects the calibration, a recalibration is necessary each time the membrane seal is broken. For this reason, the sample cell 12 has a cover 44 that allows sample and cantilever exchange without disturbing the membrane 14 The cover 44 may be sealed to the sample cell 12 with an o-ring. The cell volume is variable, depending on sample thickness, but can be on the order of several hundred microliters ($\mu$l). An inlet port 48 and outlet port 50 permit the flow of gas or liquid through the cell 12 and sample environment 43. Ports may also be provided for various monitoring devices or probes, such as a pH monitor or a temperature transducer (e.g., thermocouple) to monitor the temperature in the cell.

A sample 62 is mounted within the sample cell 12 on a sample mount 52, which is typically a disk with wire clips. The sample mount and clips can be made of passivated metal (e.g., titanium) or gold. A threaded post connects the sample mount 52 to the backing plate 40, which compresses the membrane 14 between the two disks 52,40. This compression seal need not be sufficient to maintain a >1 atm pressure differential; it is only needed to prevent liquid from leaking into the gas pressurized part of the base chamber 10 by gravitation. An optical window 54 (e.g., sapphire) is fitted over an opening in the sample cell cover 44 with an o-ring seal and a retaining ring (stainless steel). A protective cover 56 may be provided for the window 54. A cantilever-tip assembly 58 is held in place on the cover 44, such as by a laser-welded titanium clip.

Careful choice of materials is important for both thermal stability and corrosion resistance. The materials in the sample cell 12 must not significantly corrode or dissolve. Among other problems, incompatible materials could lead to "poisoning" of experiments. Passivated (oxidized) titanium is an optimal material for hydrothermal experimentation because of its corrosion resistance. Therefore, almost all parts that are in contact with the fluid are made of titanium, with the exceptions of the optical window 54, the microfabricated cantilever-tip assembly 58, and the flexible membrane 14.

If the sample is heated, heat loss from the sample cell 12 takes place through radiative and convective heat loss to air, and conductive heat flow through microscope components.

Conductive loss is minimized by inserting the insulating spacer 42 between the sample cell 12 and the base chamber 10, and by using screws made of relatively low thermal conductivity to fasten the sample cell 12 through the insulating spacer 42 to the base chamber 10. Heating means are used to heat the sample cell 12 and maintain the desired temperature. For example, referring to FIG. 2, a pyrophyllite booster heater ring 60 may be used that fits snugly around the sample cell 12 with resistive heating wire (e.g., nichrome) woven-wrapped through the ring 60. Minimal lateral thermal drift has been encountered with this technique.

Figure 3:
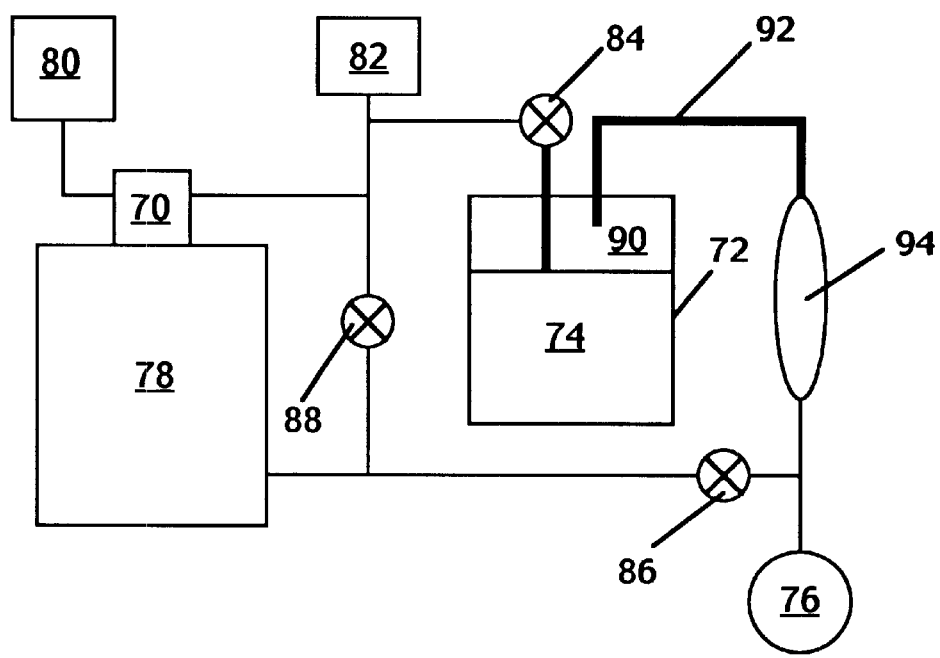
FIG. 3 shows an embodiment of a pressurized solution reservoir with the tubing and valve system.

FIG. 3 shows a schematic of the tubing and valve system for the AFM. In this embodiment, a pressurized liquid 74 flows through the sample cell 70. The fluid 74 is contained in a hydrothermal solution source reservoir 72, such as a hydrothermal bomb (e.g., PARR Instrument Co.). The source 72 is pressurized by the same gas supply 76 (e.g., $N_2$ or Ar) that pressurizes the base chamber 78 of the microscope. This approach ensures that the selected pressure in the base chamber 78 and in the sample cell 70 environment are substantially the same. The solution 74 in the source 72 may be overheated in order to degas it and thus prevent exsolution and bubble formation in the sample cell 70 and fluid supply lines. This requires that the pressure limits of the system be somewhat higher than required by the vapor pressure of the liquid (e.g., water) at a given sample cell temperature. Flow rate may be controlled using a mass flow controller 80 (e.g., Porter Instrument Co.); a dome-type back pressure regulator 82 may be used as a safety relief valve.

It is important to be able to quickly isolate the large thermal mass of the fluid source 72 from the microscope. A catastrophic problem (such as a system leak or a break in the membrane) could destroy much of the microscope if flow cannot be stopped or if pressure between the base chamber 78 and sample cell 70 cannot be equalized. Closing valves 84 and 86 isolates the source 72 and the gas pressurization from the microscope. Subsequent opening of valve 88 makes use of an expanding gas to expel remaining fluid either through the back pressure regulator 82 or through the flow controller 80. The parameters controlling both of these regulation devices can be changed quickly.

The vapor 90 above an aqueous solution 74 in the source 72 is steam. Water vapor may be diffused back out through the gas inlet, and condense on the tubing walls 92. A drying column 94 may be used to ensure that no fluid collects (condenses) in the gas-filled tubing 92 and enters the microscope base chamber 78. The electrical components in the pressurized base chamber 78 must be kept dry.

Figure 4:
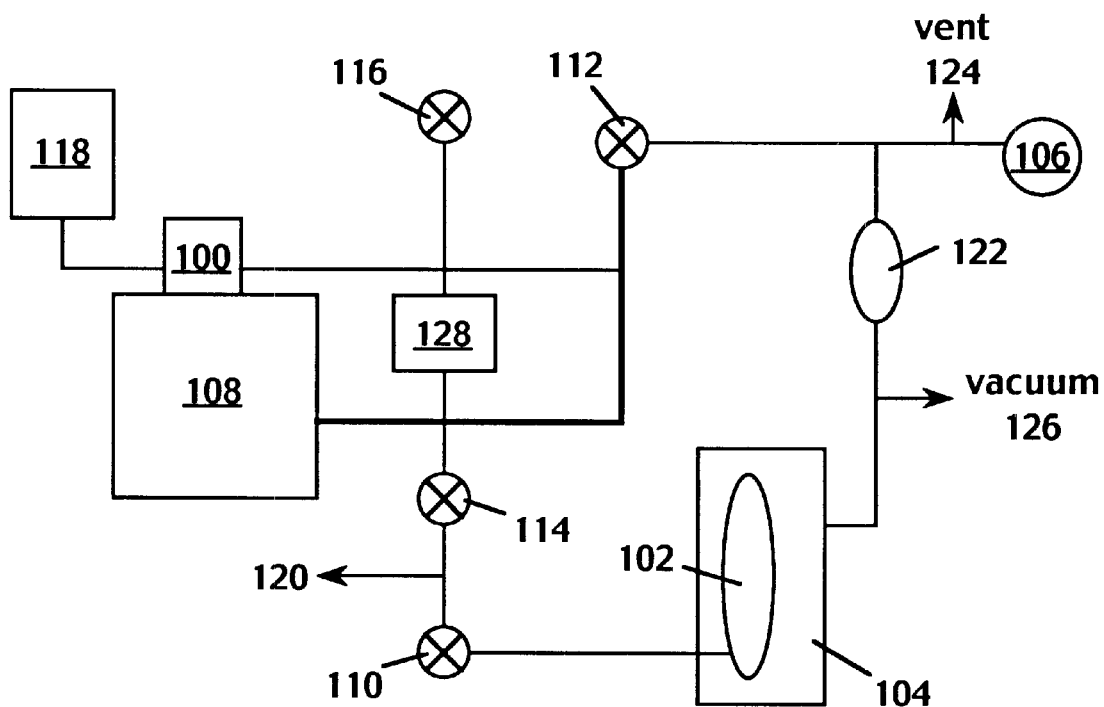
FIG. 4 shows an alternative embodiment of the solution reservoir with tubing and valve system.

FIG. 4 shows another embodiment of the fluid reservoir and tubing and valve system that has been developed. A bladder 102 serves as a source reservoir for the pressurized liquid that is fed into the sample cell 100. The bladder 102 is contained in a pressure vessel 104 and pressurized by the same gas supply 106 that pressurizes the base chamber 108 of the microscope. The solution in the bladder 102 is degassed to prevent exsolution and bubble formation in the sample cell 100 and fluid supply lines.

As mentioned above, in the event of a problem, the fluid source 102 must be isolated from the microscope. Closing valves 1110 and 112 isolates the bladder 102 and the gas pressurization from the microscope. Subsequent opening of valve 114 makes use of an expanding gas to expel remaining fluid either through a relief valve 116 or through a flow controller 118. An additional valve 120 can be used to bleed the system and may be used to feed liquid to the bladder 102.

The fluid in the bladder 102 is isolated, and therefore vapor is less likely to condense on the tubing walls than in the system shown in FIG. 3. However, to protect against any vapor reaching the electrical components in the base chamber 108 a drying column 122 may be used. The system may also include valves in the gas lines for a vent 124 and connection to vacuum 126 and a pressure transducer 128 for monitoring fluid pressure.

In an alternative embodiment, the sample's environment is gaseous, not liquid, and then the same gas source 106 can be used to pressurize the base chamber 108 and the sample cell 100. Without the liquid reservoir and threat of condensation in the supply lines, the design of the valve and tubing system is simplified.

Although there is equal pressure in the base chamber and the sample cell on both sides of the membrane, gas from the base chamber may diffuse through the membrane to the liquid in the sample cell and create bubbles. For this reason, the membrane material is chosen to limit such diffusion, and the inert gas in the base chamber is typically nitrogen or argon, which cannot easily diffuse through the membrane. Helium atoms, however, are small and more likely to permeate the membrane. To further isolate the sample cell from the base chamber, an alternative design of the microscope was developed.

Figure 5:
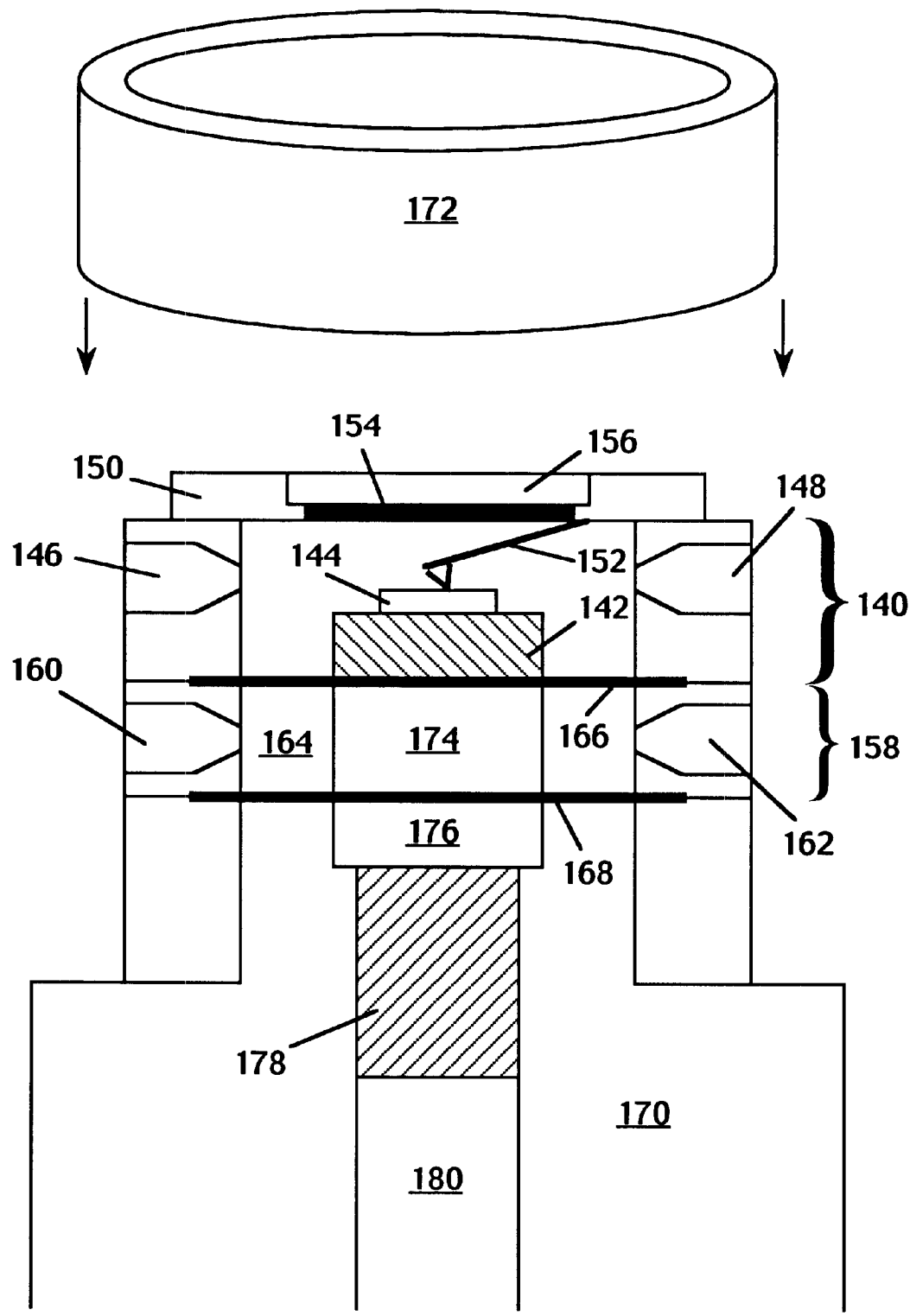
FIG. 5 shows an alternative embodiment of the hyperbaric AFM with two stacked fluid cells.

FIG. 5 shows an alternative embodiment of the AFM with two stacked fluid cells 140,158. The upper cell 140 is the sample cell, the same as described for FIG. 2, with sample mount 142 for sample 144, a fluid inlet 146 and outlet 148, a cover 150 with cantilever-tip assembly 152, an optical window 154 and window cover 156. The lower cell 158 is a fluid cell having an inlet 160 and outlet 162 to allow the flow of fluid through the cell chamber 164. Two membranes 166,168 are situated between the sample cell 140 and the base chamber 170. The pressurized gas in the base chamber is thus prevented from reaching the sample cell 140 by the two membranes and by the flow of fluid through the lower cell 158. The purpose of the lower cell 158 is to sweep away any gases that permeate through the lower membrane 166 before reaching the sample cell 140. The fluid in the lower cell 158 is always kept devoid of gas, which prevents bubbles from forming in the upper cell 140.

Support means 174 are situated in the fluid cell 158 between the membranes 166,168 to support the overlying sample mount 142 (and couple to the piezoelectric scanner 180 in the base chamber 170), yet still allow the flow of fluid through the cell chamber 164. The support means 174 are positioned on top of a backing plate 176 and spacer 178 in the base chamber 170. The same insulating spacers can be employed as described for FIG. 2. If the sample is heated, heating means 172 are placed in thermal contact with the sample cell 140 and preferably also with the lower fluid cell 158.

It is apparent to one skilled in the art that the flow of pressurized fluid can be achieved in both cells 140,158 using systems analogous to those shown in FIGS. 3–4. The fluid flowing through the lower cell 158 may be, but need not be, the same as the fluid passing through the sample cell 140. The flow of pressurized fluid, either liquid or gas, from the fluid reservoir can be split into two lines leading to the two cells; fluid flow may be monitored by multiple flow controllers.

The hyperbaric AFM has been tested under hydrothermal conditions to produce images of solid surfaces in aqueous solutions at high temperature and pressure. Images of $CaCO_3$ (1014) were taken under static (non-flow) conditions in water at temperatures of 127° C. and 143° C. Based on a two-point vertical calibration at 180 nm and 335 nm, the steps shown in these images are 0.3 to 0.4 nm high, which is near the expected 0.3 nm height of single-layer steps on this surface. An indication of lateral calibration, albeit a relative one, is the measured rhombohedral angle of 111°, which compares favorably to the 102° angle expected for this surface. In addition, images of a hematite ($\alpha$-$Fe_2O_3$) (0001) surface show that fluid flow at a rate of 0.25 mL/min does not substantially disturb imaging. The tolerances of the hyperbaric AFM with regard to fluid flow are not significantly different from those of an ambient AFM.

Changes in piezoelectric tube scanner sensitivity with increasing gas pressure have been measured, and the sensitivity change is such that there is apparently less resistance to scanning at high pressures than at ambient pressure. That is, at higher pressures, the actual scanned distances increase. Scanner sensitivity as a function of temperature has also been measured, and the piezoelectric scanner also scans larger distances at higher temperatures. Changes are substantial with heating to 50° C., but the sensitivity between 110° C. and 130° C. is independent of temperature. Scanner sensitivity is a sufficiently strong function of pressure and temperature that calibration under the conditions to be studied, specific not only to the scanner but also to a particular membrane installation, is important for accurate distance measurements.

The novel design of this AFM achieves several important objectives. This AFM permits in-situ contact imaging in gas or liquid (e.g., aqueous solution) at pressures greater than ambient pressure and at temperatures above the boiling temperature of the sample solution (e.g., >100° C. for aqueous solutions). The AFM allows routine single atomic-layer vertical resolution in-situ under the above conditions with control of temperature, pressure and fluid flow rate during imaging. This system is relatively easy and safe to use. The need for new hardware design has been minimized, i.e., commercial scanning control and optical systems are used.

The foregoing description of preferred embodiments of the invention is presented for purposes of illustration and description and is not intended to be exhaustive or to limit the invention to the precise form disclosed. Many modifications and variations are possible in light of the above teaching.

What is claimed is:

1. An atomic force microscope for imaging a surface of a sample at a selected pressure greater than atmospheric pressure, comprising:
   a base chamber for containing a pressurized gas at the selected pressure;
   a sample cell operably connected to the base chamber and having a chamber for containing a pressurized fluid at the selected pressure;
   said sample cell comprising an inlet port and an outlet port for introducing and discharging the pressurized fluid from the sample cell chamber,
   a flow controller to control a flow of the pressurized fluid through the sample cell,
   a membrane separating the sample cell chamber and the base chamber;
   a sample mount for mounting the sample in the sample cell;
   a probe for tracing the surface of the sample,
   a fluid cell situated between the sample cell and the base chamber, the fluid cell having a chamber for containing a pressurized fluid at the selected pressure; and
   a second membrane separating the fluid cell chamber and the base chamber.

2. The microscope as recited in claim 1, further comprising heating means for heating the sample cell.

3. The microscope as recited in claim 1, wherein the membrane comprises a flexible, chemically inert material.

4. The microscope as recited in claim 1, further comprising a backing plate, wherein the membrane is situated between the sample mount and the backing plate.

5. The microscope as recited in claim 1, wherein the base chamber comprises scanning means for scanning the sample and an insulating scanner spacer, wherein the scanner spacer is situated between the sample cell and the scanning means.

6. The microscope as recited in claim 1, wherein the sample cell comprises a cover having an opening for an optical window.

7. The microscope as recited in claim 1, further comprising an insulating spacer adjacent the sample cell, wherein the membrane is situated between the sample cell and the insulating spacer.

8. The microscope as recited in claim 1, further comprising a reservoir of pressurized fluid connected to the sample cell.

9. The microscope as recited in claim 1, further comprising at least one flow controller to control fluid flows through the sample cell and the fluid cell.

10. A method for imaging a surface at a selected pressure greater than atmospheric pressure using an atomic force microscope having a probe for tracing the surface of a sample, comprising:
    mounting the sample in a sample cell operably connected to a base chamber and having a chamber containing a pressurized fluid at the selected pressure, wherein the sample cell chamber and the base chamber are separated by a membrane;
    pressurizing the base chamber with a pressurized gas at the selected pressure;
    introducing the fluid into the sample cell chamber;
    flowing the fluid through the sample cell;
    maintaining the gas pressure in the base chamber and the fluid pressure in the sample cell chamber at substantially the same selected pressure;
    tracing the surface of the sample with the probe; and
    providing a fluid cell situated between the sample cell and the base chamber, the fluid cell having a chamber for containing a pressurized fluid at the selected pressure, and wherein the fluid cell chamber and the base chamber are separated by a second membrane.

11. The method as recited in claim 10, further comprising heating the sample cell.

12. The method as recited in claim 11, wherein the fluid is heated above about 100° C.

13. The method as recited in claim 10, wherein the fluid comprises a liquid.

14. The method as recited in claim 10, further comprising providing a reservoir of pressurized liquid connected to the sample cell.

15. The method as recited in claim 10, further comprising thermally insulating the sample cell from the base chamber.

16. The method as recited in claim 10, further comprising flowing fluid through the fluid cell.

* * * * *